(12) United States Patent
Al-Hoshani

(10) Patent No.: US 10,324,223 B2
(45) Date of Patent: Jun. 18, 2019

(54) METHOD, AN APPARATUS, AND A SYSTEM FOR AUTOMATED INSPECTION OF MOTORIZED VEHICLES

(71) Applicant: Mohammed Al-Hoshani, Riyadh (SA)

(72) Inventor: Mohammed Al-Hoshani, Riyadh (SA)

( * ) Notice: Subject to any disclaimer, the term of this patent is extended or adjusted under 35 U.S.C. 154(b) by 180 days.

(21) Appl. No.: 14/596,035

(22) Filed: Jan. 13, 2015

(65) Prior Publication Data

US 2015/0369955 A1    Dec. 24, 2015

Related U.S. Application Data

(63) Continuation of application No. PCT/US2014/043751, filed on Jun. 24, 2014.

(51) Int. Cl.
*G01T 1/16* (2006.01)
*G01V 5/00* (2006.01)
(Continued)

(52) U.S. Cl.
CPC ........... *G01V 5/0016* (2013.01); *G01N 23/10* (2013.01); *G01N 35/02* (2013.01); *G01T 1/1603* (2013.01);
(Continued)

(58) Field of Classification Search
CPC ........ G01N 23/00; G01N 23/02; G01N 23/04; G01N 23/06; G01N 23/08; G01N 23/083; G01N 23/10; G01N 2223/00; G01N 2223/03; G01N 2223/04; G01N 2223/10; G01N 2223/101; G01N 2223/1013; G01N 2223/1016; G01N 2223/30; G01N 2223/33; G01N 2223/3307; G01N 2223/3308; G01N 2223/40; G01N 2223/60; G01N 2223/639; G01N 2223/643; G01N 23/087; G01N 23/18; G01N 2223/306; G01N 2223/308;
(Continued)

(56) References Cited

U.S. PATENT DOCUMENTS 4,599,740 A * 7/1986 Cable ................... G01V 5/0016
378/57
5,065,418 A * 11/1991 Bermbach ............ G01V 5/0016
250/358.1
(Continued)

OTHER PUBLICATIONS

Kazuo Takei, "Cargo Container X-ray Inspection System", Jun. 2004, Hitachi Ltd, Hitachi Reviews, Physical Security, vol. 53, No. 2, pp. 97-102.*

*Primary Examiner* — Anastasia Midkiff
(74) *Attorney, Agent, or Firm* — Oblon, McClelland, Maier & Neustadt, L.L.P.

(57) ABSTRACT

A method, an apparatus, and a system for x-ray scanning inspection of motorized vehicles are described. The apparatus or system comprises a concrete facility that has a concrete housing, multiple x-ray beam sources, multiple x-ray beam detectors on respective opposite sides of the multiple x-ray beam sources, and a conveyor belt. The apparatus or system is automated to deliver alerts if any of the scanned motorized vehicles contain prohibited materials. The method, apparatus, and system are able to detect organic versus inorganic matter. Specific beam strength and a distance between the motorized vehicles make this technology automated and more accurate for security screening of a large number of motorized vehicles.

15 Claims, 8 Drawing Sheets

(51) Int. Cl.
*H05G 1/02* (2006.01)
*G01N 23/10* (2018.01)
*G01N 35/02* (2006.01)
*G01N 35/04* (2006.01)
*G01N 23/087* (2018.01)

(52) U.S. Cl.
CPC ............ *G01V 5/0041* (2013.01); *H05G 1/02* (2013.01); *G01N 23/087* (2013.01); *G01N 2035/0489* (2013.01); *G01N 2035/0491* (2013.01); *G01N 2223/308* (2013.01); *G01N 2223/3307* (2013.01); *G01N 2223/643* (2013.01); *G01N 2291/011* (2013.01); *G01N 2291/2698* (2013.01)

(58) Field of Classification Search
CPC .... G01N 2223/66; G01N 35/02; G01N 35/04; G01N 2035/0474; G01N 2035/0482; G01N 2035/0484; G01N 2035/0489; G01N 2035/0491; G01N 2291/00; G01N 2291/01; G01N 2291/011; G01N 2291/26; G01N 2291/269; G01N 2291/2698; G01T 1/00; G01T 1/16; G01T 1/1603; G01T 7/00; G01T 7/08; E04H 6/00; E04H 6/08; E04H 6/12; E04H 6/30; E04H 6/302; E04H 6/32; G01V 5/00; G01V 5/0008; G01V 5/0016; G01V 5/0041; H05G 1/00; H05G 1/02
See application file for complete search history.

(56) References Cited

U.S. PATENT DOCUMENTS

| | | | | |
|---|---|---|---|---|
| 5,524,133 | A * | 6/1996 | Neale | G01N 23/04 250/393 |
| 6,542,580 | B1 * | 4/2003 | Carver | G01N 23/04 378/57 |
| 2008/0014643 | A1 * | 1/2008 | Bjorkholm | G01N 23/04 436/57 |
| 2009/0147913 | A1 * | 6/2009 | Dragon | G01V 5/0016 378/57 |
| 2011/0064192 | A1 * | 3/2011 | Morton | G01V 5/0016 378/57 |
| 2011/0142201 | A1 * | 6/2011 | Eberhard | G01V 5/0008 378/57 |
| 2012/0076257 | A1 * | 3/2012 | Star-Lack | G01V 5/005 378/4 |
| 2012/0148019 | A1 * | 6/2012 | Johnson | G01V 5/0016 378/57 |

* cited by examiner

METHOD, AN APPARATUS, AND A SYSTEM FOR AUTOMATED INSPECTION OF MOTORIZED VEHICLES

CROSS REFERENCE TO RELATED APPLICATION

The instant application is a 371 national stage of international application no. PCT/US14/43751 filed on Jun. 24, 2014. The content of PCT/US14/43751 is hereby incorporated by reference in its entirety.

FIELD

This disclosure relates generally to a method, an apparatus, and a system to inspect automatically a motorized vehicle. More specifically, embodiments of the invention can enable automatic performance of an inspection of one or more motorized vehicles using a high energy x-ray source from multiple dimensions.

BACKGROUND

Worldwide trade and movement of goods via sea, land, and vehicular traffic poses a technical challenge to inspect contents in an efficient, secure, and fast manner. Carver et. al. (U.S. Pat. No. 6,542,580) describes a relocatable x-ray imaging system. The x-ray system is fixed on the top and low energy x-rays are used for scanning the objects. There are several other drawbacks in the prior art, such as lack of a rolling conveyor belt system to move the vehicles, lack of horizontal leveling, weakness of x-ray penetration capacity due to use of low energy x-rays, and radiation exposure to the users. If low energy x-rays are used, the inspection may fail and may have to be repeated, for instance, manually.

SUMMARY

The current disclosure is directed to a method, an apparatus, and a system for automatic inspection of motorized vehicles (e.g., cars, vans, trucks, etc.) using at least one x-ray. In one embodiment of the present disclosure, an apparatus or system can comprise a concrete enclosure, and a conveyor belt in the concrete enclosure to move a motorized vehicle at a specific speed for a security inspection. In one embodiment, a method can comprise discharging a first x-ray beam using a first x-ray beam source mounted at a side of the conveyor belt, inside the concrete enclosure, and discharging a second x-ray beam using a second x-ray beam source mounted on the roof of the concrete enclosure (but inside the concrete enclosure), at the motorized vehicle (and/or an object therein or thereon) at a specific angle, a specific direction, and a specific range to detect a specific object, material, or contraband, for instance, that is or may be a security threat.

In one embodiment, a method can be comprised of passing a motorized vehicle through a concrete housing equipped with a two x-ray imaging system to screen for an organic or an inorganic matter that may be present in the motorized vehicle, or an object that is prohibited by law enforcement; and activating the two x-ray imaging system at a specific range to penetrate a specific thickness of the motorized vehicle to detect whether the organic or inorganic material or the object is present in the motorized vehicle.

In another embodiment, the conveyer belt can be made of rubber and enhanced steel having two longitudinal sections that are 5 mm apart, for instance, to allow the x-ray to pass through motorized vehicles for inspection. The specific speed of the motorized vehicle(s) moving on the conveyor belt can be between 0.1 m/sec. to 0.3 m/sec., wherein the specific speed, in one specific embodiment, is 0.2 m/sec. In another embodiment, the specific range for the x-ray beam is between 3.8 MeV to 6 MeV. In one embodiment, the specific thickness for the body of the motorized vehicle may be between 0-240 mm.

In one embodiment, the apparatus, the system, and the method of automated inspection provides means for differentiating between organic matter and inorganic matter. This method can be useful to detect contraband in motorized vehicles in closed or sealed parcels.

The apparatus, method, and system, as disclosed, can implement a two x-ray imaging system, which may be comprised of a first x-ray imaging apparatus and a second x-ray imaging apparatus. The first x-ray imaging apparatus can include a first x-ray beam source and can be mounted on a side of a conveyor belt inside a concrete enclosure, and the second x-ray imaging apparatus can include a second x-ray beam source on the roof of the concrete enclosure. The x-ray beams from the first x-ray beam source and the second x-ray beam source can be discharged at respective specific angles so that the x-ray beams intersect each other and a full scan of the motorized vehicle (including an object therein or thereon) can be performed. In one embodiment, the conveyor belt can be used to move the motorized vehicles for processing according to an inspection method. Since the motorized vehicle can be moved via the conveyor belt, the individual occupants may not be in the motorized vehicle for the inspection, which may reduce radiation exposure to individuals. In another embodiment, a detector can be located to capture the passing the x-ray beams from each of the first and second x-ray beam sources. At least one of the detectors may be located under the conveyor belt.

In one embodiment, a system can scan a license plate as soon as a motorized vehicle reaches an entry point to record license plate information. The license plate information can be updated on the system and verified. Once the method of scanning using the x-ray beams is completed, then the entire data can be stored in a database for that particular security scan.

The method, system, and apparatus disclosed herein may be executed to inspect an object inside or on a motorized vehicle, for instance, to determine whether the object constitutes organic or inorganic matter. Other features will be apparent from the accompanying drawings and from the detailed description that follows.

BRIEF DESCRIPTION OF THE DRAWINGS

Example embodiments are illustrated by way of example and not limitation in the figures of the accompanying drawings, in which like references indicate similar elements and in which.

Other features of the present embodiments will be apparent from the accompanying drawings and from the detailed description that follows.

DETAILED DESCRIPTION

Methods, apparatuses, and systems for automatic inspection of motorized vehicles for unfavorable items are described herein. Although the present embodiments have been described with reference to specific example embodiments, it will be evident that various modifications and changes may be made to these embodiments without departing from the broader spirit and scope of the various embodiments.

Figure 1:
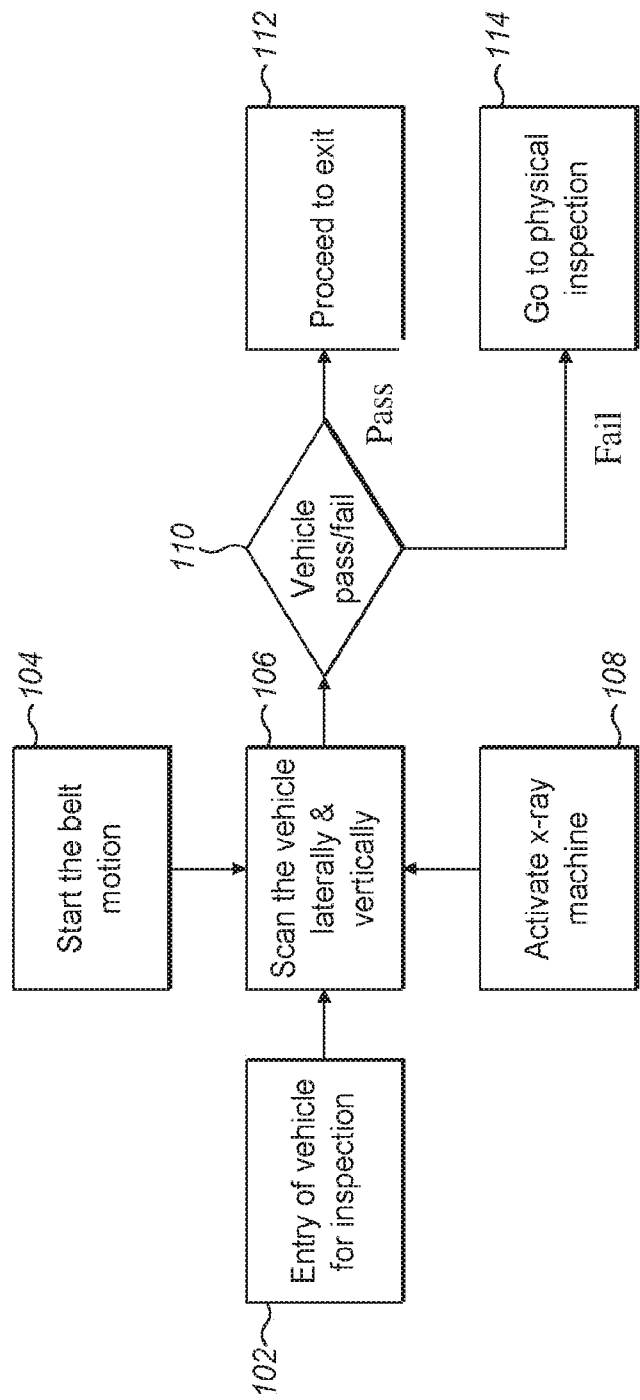
FIG. 1 shows a method for inspecting motorized vehicles according to one or more embodiments of the disclosure.

FIG. 1 shows a method for inspecting motorized vehicles according to one or more embodiments of the disclosure. In one embodiment, the method can include entry of the motorized vehicle for inspection 102, for instance, observed by an inspector at an entry room of an inspection facility, which may include a concrete enclosure. License plate information can be captured using a video camera, for instance, to collect data about the motorized vehicle and motorized vehicle's ownership. Once the motorized vehicle is cleared for entry, a conveyor belt can be started 104 for the motorized vehicle to move forward. If the item to be scanned is an object other than a motorized vehicle and does not have a license plate (e.g., a package), a bar code or any other identification process can be used for authentication before the scan is started. The conveyor belt may accommodate a motorized vehicle weight of up to 5 tons, for instance. A two x-ray imagining system with two x-ray beam sources and respective x-ray beam outputs can be activated 108 to perform a lateral scan and a vertical scan of the motorized vehicle, for instance, once the motorized vehicle reaches a center of the inspection facility. Based on the x-ray imaging, the method can determine whether the motorized vehicle (or an object inside or thereon) has passed the security check or has failed the security check 110. If the conclusion is that the motorized vehicle has passed the security check, then the motorized vehicle proceeds towards an exit 112 of the inspection facility. If there is any suspicion and the motorized vehicle has not passed the security check, then the motorized vehicle goes over to another enclosure for further physical inspection 114.

Figure 2:
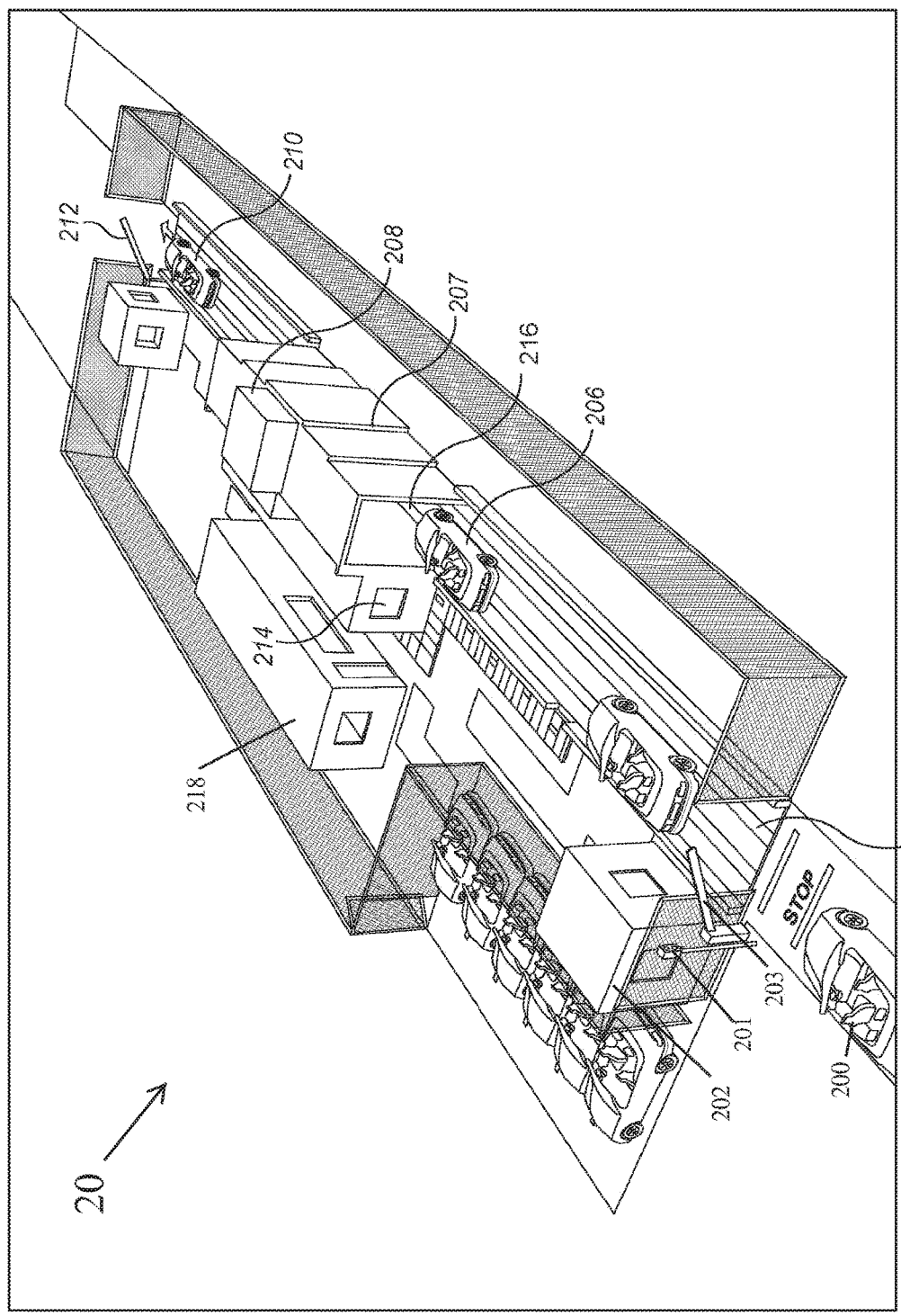
FIG. 2 is a perspective view of an example of a concrete enclosure of an inspection facility to conduct an inspection of motorized vehicles, according to one or more embodiments of the disclosure.

FIG. 2 is a perspective view of an inspection facility 20 to conduct an inspection of motorized vehicles, according to one or more embodiments of the disclosure. Generally, the inspection facility 20 can be comprised of a concrete enclosure 214, a vehicle identification mechanism, a conveyor belt 216, a two x-ray imaging system configured to scan all portions of a motorized vehicle desired to be scanned, one or more image analysis computers, x-ray detectors, and equipment to protect persons from radiation exposure. A motorized vehicle, for instance, a car 200, approaches a gate 203 at an entryway of the inspection facility 20. A picture of the license plate of the car 200 can be taken from a camera 201. An inspector in the entry room 202, for instance, waits for the system to provide information about the details of the car 200 based on the picture of the license plate. The system can tie the information about the security check to the car 200 and the person that owns the car 200. For example, there might be a history of security checks, and if there are any flags, then the inspector may consider not letting the car 200 be inspected. There may be other means of scanning the car 200, such as a vehicle identification number, a bar code, a package number, and a license plate number to further determine the legitimacy of the car 200. The method, system, and apparatus, according to embodiments of the disclosure, may be installed in front of dignitary houses, large hotels, important gathering places, large assemblies of people such as concerts, game centers, ports, airports, railway stations, and any other transportation areas.

Figure 4:
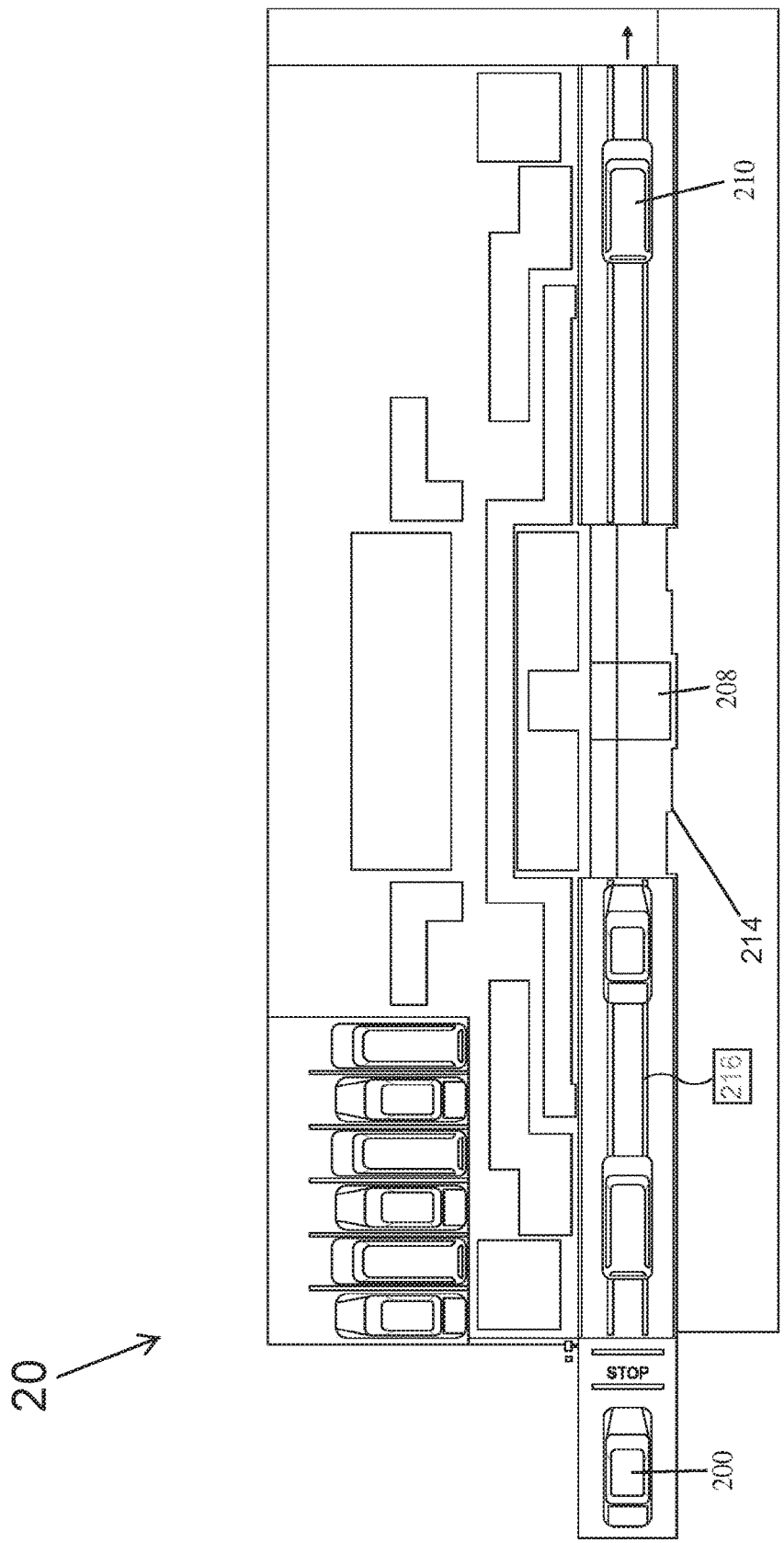
FIG. 4 is a top plan view of the inspection facility of FIG. 2.

The car 200 can reach an entry point 206 of the concrete enclosure 214 via movement on the conveyor belt 216, and can then be moved on the conveyor belt 216 inside a tunnel formed by the concrete enclosure 214, including thick concrete walls 207. The conveyor belt 216 may be a double-belt conveyor, such as shown in FIGS. 2 and 4. A top x-ray beam source 516 can be housed at or in a roof 208 of the concrete structure 214. A side x-ray beam source 506 can be housed in the concrete enclosure 214 beside or adjacent to the conveyor belt 216. A detector 512 may be associated with the side x-ray beam source 506. A first x-ray imaging apparatus may be comprised of the side x-ray beam source 506 and the detector 512. A detector 514 may be associated with the top x-ray beam source 516. A second x-ray imaging apparatus may be comprised of the top x-ray beam source 516 and the detector 514. One or more inspectors may work in an image analysis room 218. The people who are travelling in the car 200 may be asked to disembark and use the side walk 620 (shown in FIG. 6). FIG. 2 shows that cars, such as car 200 and car 210, can be continually screened in one line. Car 210 has already passed inspection and is shown proceeding to a gate 212 that may be provided at an exit of the inspection facility 20.

Figure 3:
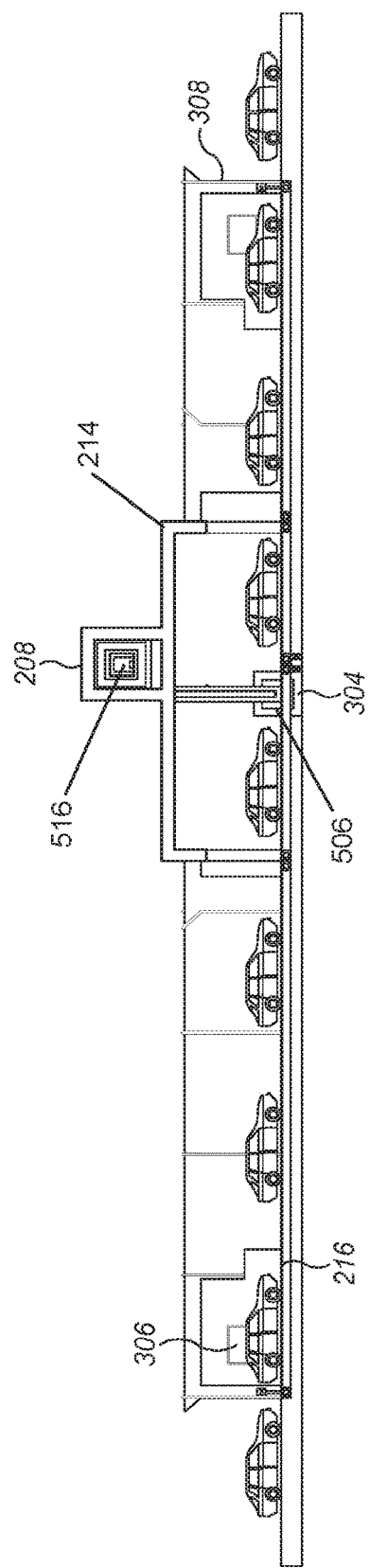
FIG. 3 is a side sectional view of the inspection facility of FIG. 2 showing how rows of motorized vehicles may enter and exit the inspection facility.

FIG. 3 is a side sectional view of the inspection facility 20 of FIG. 2 showing how rows of motorized vehicles, cars in this case, may enter and exit the inspection facility. The cars are moving on the conveyor belt 216. One of the cars has a cargo 306 on top. Once each of the cars reaches the scanning point 304, the top x-ray beam source 516, which may be in the roof 208 of the concrete enclosure 214, and the side x-ray beam source 506, which may be beside or adjacent to conveyor belt 216 of the concrete enclosure 214, can be controlled to activate and discharge respective x-ray beams toward the car at the scanning point 304, and the respective two detectors 514, 512 can capture the output of the top x-ray beam source 516 and the output of the side x-ray beam source 506, once passed through the car, to generate x-ray imagery of the car for further analysis. All of the procedures are completed before each car reaches the exit point 308. Based on the image analysis results it is decided if the car needs further physical scrutiny, otherwise the car will be allowed to get out of the concrete enclosure 214 after an issuance of a cleared pass permit.

FIG. 4 is a top plan view of the inspection facility 20 of FIG. 2. Car 200 enters the gate 302 after the license plate and back ground check, and in arranged on conveyor belt 216. (This particular figure shows the concrete enclosure 214 that houses top x-ray beam source 516, which may be provided in the roof 208 of the concrete enclosure 214, and the side x-ray beam source 506, which may be arranged beside or adjacent to the conveyor belt 216 of the concrete enclosure 214, is in a secure building so that personal may not be exposed to radiation while the car 200 is being inspected. Once the radiation inspection of the car 200 is finished, at position 210, the car may go for either manual inspection or is cleared to exit, depending upon the results of the scanning. The system is tied to the method of security inspection of the car 200. The data from the entry point such as the car identification, owner information, paper connected with passage (such an invitation, customs form for the list of goods, etc.) can be correlated in a database using a wireless network and displayed on a computer of the inspection facility 20. Once the inspection is done, a time and a date stamp can be attached, and the image of the inspection can be linked to the car 200. If there is any suspicion, then the authorities can be alerted automatically. The radiation levels can be constantly monitored so that the cumulative exposure is not exceeded for inspection personnel. The data accumulated may be shared with all the pertinent departments, such as security, police, customs, national security, etc. Alerts of security breach may also be automated instead of manual entry.

Figure 5:
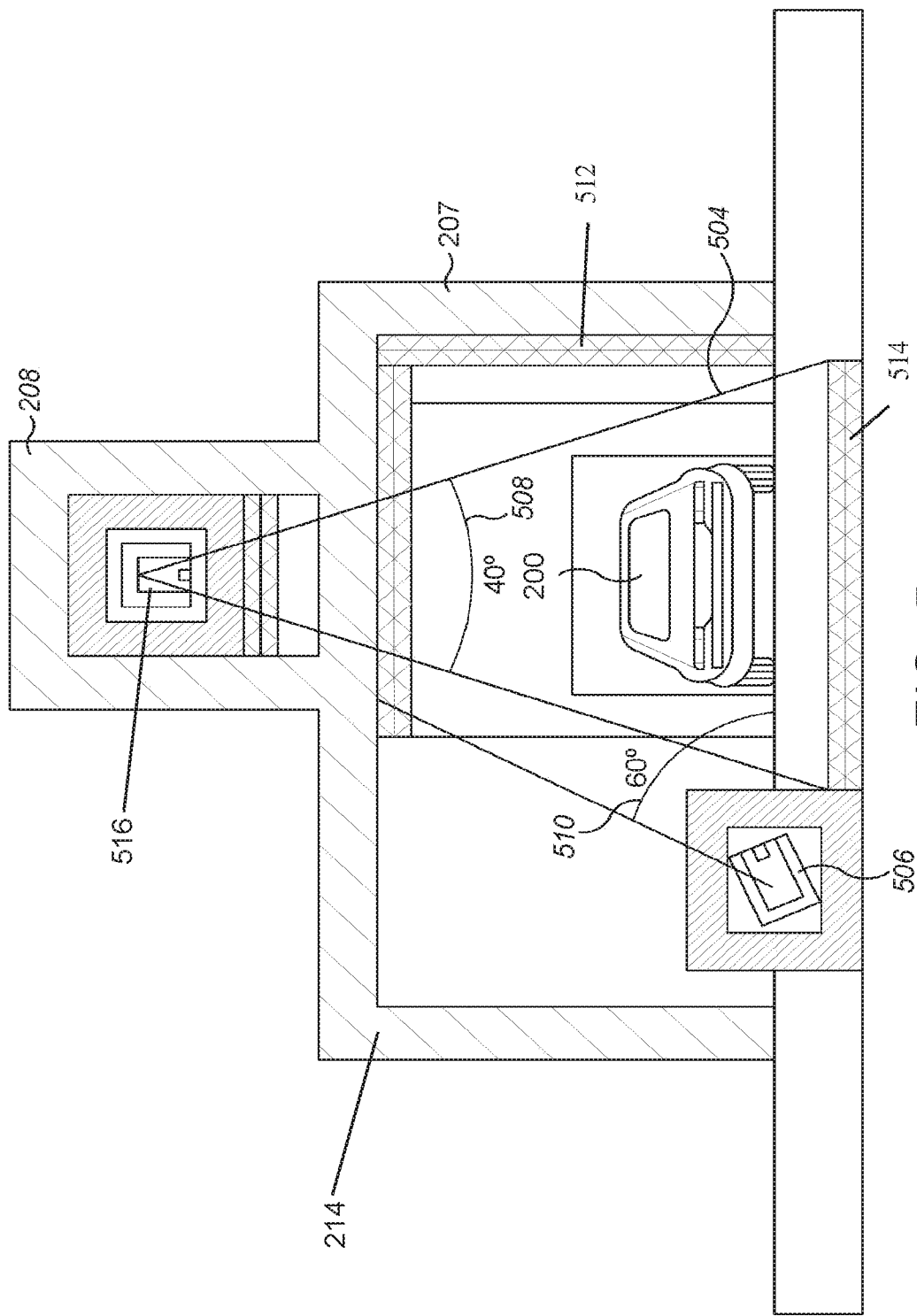
FIG. 5 is a cross-sectional view of a portion of the inspection facility of FIG. 2.

FIG. 5 is a cross-sectional view of a portion of the inspection facility 20. The x-ray beam from the top x-ray beam source 516 can be caused to diverge at a specific angle 508 toward the car 200. For example, the top x-ray beam may diverge so as to form a beam that spans an angle of 40 degrees, such as shown in FIG. 5. The top x-ray beam source 516 can be positioned above the car 200 and have a beam divergence 508, such that a bottom portion of the beam 504 has a predetermined width to cover the entire car 200 (including an object thereon) from top to bottom. The concrete enclosure 214 can have a thick wall, such as concrete outer enclosure 207, and an L shape detector 512 to gather the emitted x-ray beams from the side x-ray beam source 506. The beams from the top x-ray beam source 516 can be recorded by a detector 514, which may be under the conveyor belt 216. The signal from the detector 514 can be recorded and analyzed to approve the car 200 (or object therein or thereon) to be clear or to be analyzed for further inspection. The beam angle 510 for the x-ray beam of the side x-ray beam source 506 can be diverged at a 60 degree angle, for instance. The specific angles 508, 510 can enable the method, system, and apparatus to function efficiently, accurately, and sensitively to collect the scan data for the car 200 without missing any sections.

The beam angle of the x-rays emitted from the top x-ray beam source 516 can be 40 degrees, for instance, because the detector 514 located under the conveyor belt 216 can be shorter than from the front of the detector 512 and the side x-ray beam source 506, which can output an x-ray beam at 60 degrees, because the detector 512 has two parts, one horizontal and one vertical. The side x-ray beam source 506 can be installed diagonally so the emitted x-ray beam can penetrate the car 200 and reach the detector 512.

Figure 6:
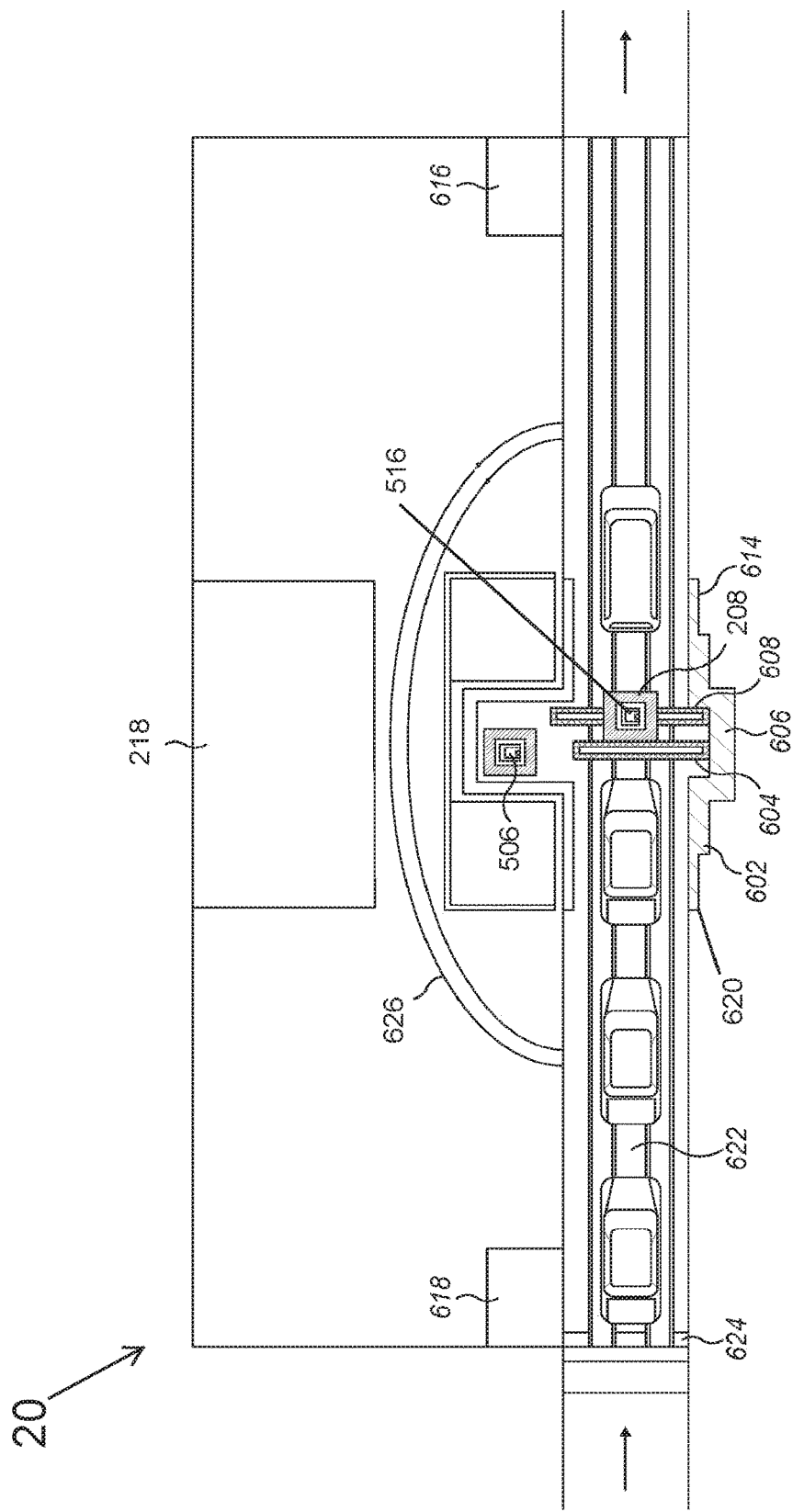
FIG. 6 is a top plan view of a portion of the inspection facility of FIG. 2.

FIG. 6 is a top plan view of a portion of the inspection facility 20. The conveyor belt 622 can be made up of rubber, and the structure can be further enhanced by steel 624. The conveyor belt 622 can be comprised of two detachable sections so that the main movement of motorized vehicles via the motorized vehicle transport system to the x-ray detection tunnel frame 602 (806) and 614 (804) can be sequentially one after another, then the motorized vehicles can be pushed out after the end of the inspection method. Such a conveyor belt 622 may be operated by motors which enhance the rotation of the conveyor belt continuously and sequentially. There may be a longitudinal vacuum 604 between the two detachable conveyor belt sections, for instance, at 5 mm, which may enable penetrating of the respective x-ray beams from the top x-ray beam source 516 and the side x-ray beam source 506 to the respective detectors 512, 514. Another longitudinal vacuum 608 may be provided. Further, one or more of the detectors 512, 514 may include a Cadmium tungstate substance, which may be located below the aforementioned longitudinal vacuum 604. The x-ray detectors 512, 514 can be located between the two conveyor belts, while there can be two penetrative x-ray sources rated from 3.8 MeV to 6 MeV. As shown in the FIG. 6, the entry point 618 is for motorized vehicles for inspection. Longitudinal vacuum 604 and longitudinal vacuum 608 are supported by a concrete base 606 of the concrete enclosure 214.

Figure 7:
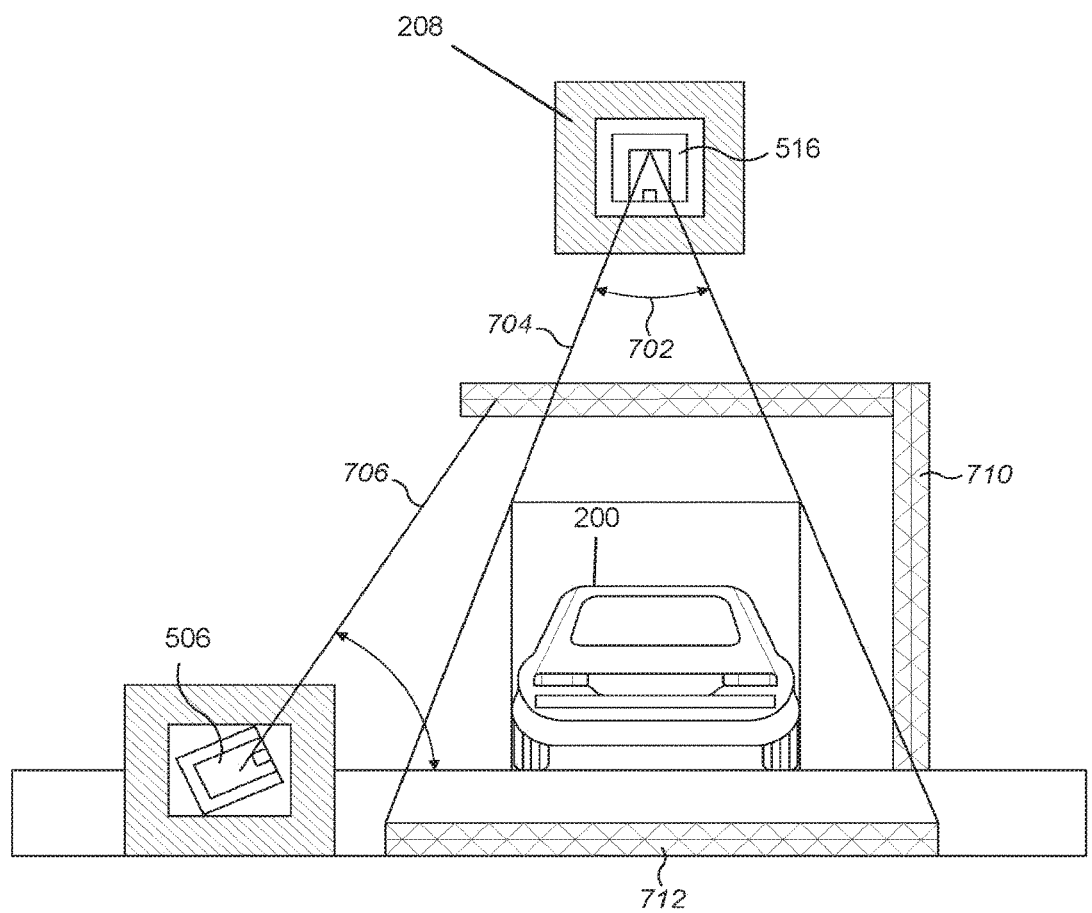
FIG. 7 is a cross-sectional view of a portion of the inspection facility of FIG. 2.

FIG. 7 is a cross-sectional view of a portion of the inspection facility 20. Notably, FIG. 7 discloses more details of the top x-ray beam source 516 and the side x-ray beam source 506 and the angles of each x-ray beam respectively output therefrom. The side x-ray beam source 506, which may be referred to as a first x-ray beam source, can be mounted next to the left side detection tunnel, whereas the related detector 710 can be at the opposite side The detector 710 take the form of an inverted L shape. The top x-ray beam source 516, which may be referred to as a second x-ray beam source, can be mounted at the roof 208 of the of the concrete enclosure 214, where the x-ray beam 704 from the second x-ray beam source 516 can be directed vertically downward to penetrate the motorized vehicle (e.g., car), and toward the detector 712, which can be mounted on the ground and below the longitudinal vacuum or vacuums. The specific angle for the top x ray beam is shown as angle 702. The side x-ray beam source 506 can have the x-ray beam 706 covering the car 200, as shown. This invention shall overcome the difficulties and the drawbacks which affected the previous systems whereas the source energy is increased (between 3.8 to 6 Me V) to get a deeper penetration up to (240 mm for the solid steel), so that one can get a clear image. Besides, there is a side source to provide a side vision of the car contents and because of the high energy of both of the x-ray sources, the scanning can distinguish between organic and non-organic materials. Also, the conveyor belt design shows that there is a continuous direction with fixed speed which increases the throughput of the motorized vehicles to be detected. Therefore, this invention shall increase the overall throughput and saving the manpower efforts along with getting clear images from the top and the side and inspecting the motorized vehicle without the need of the physical inspection or taking off the contents because of the penetrative ability.

Figure 8:
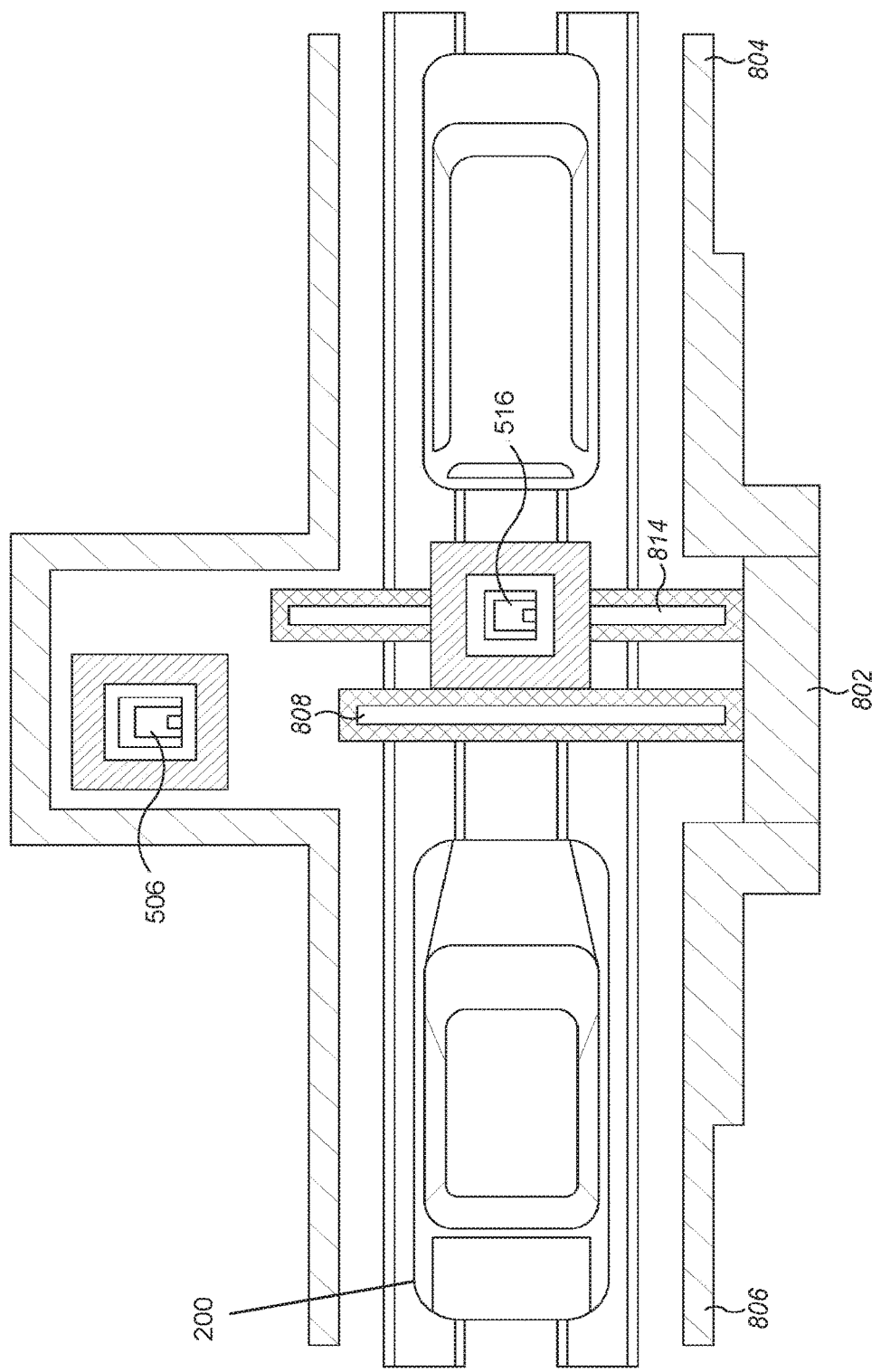
FIG. 8 is an enlarged view of a portion of FIG. 6.

FIG. 8 is an enlarged view of a portion of FIG. 6. The method can start at the time of directing the car 200 with its passengers to get into the inspection facility 20, the driver shall stop at the entry point 618 to acquire the information through a camera mounted at the entry which can capture the plate number, for instance. The acquired information can be sent to a computer connected to the information center to display the information about the driver and the car 200 on a dedicated screen for the inspector and to raise the barrier. The car 200, after it gets on the conveyor belt 622, the passengers shall leave the car 200 and walk through a safe passage 626. The inspector will control the car 200 to get into the detection tunnel 620 which comprise of concrete building enclosure 214 made up of a substance which prevents x-ray leakage. The operation of the top x-ray beam source 516 and side x-ray beam source 506 can be started to output respective x-ray beams that penetrate the body of the car 200 from the top to the bottom and then to be received by the detector 514 fixed under the longitudinal vacuum 808 and/or longitudinal vacuum 814 in a synchronous way to penetrate the body of the car 200 from the left side horizontally upward to be received by the detectors 512 fixed on the holder at the opposite side and at the upper side of the detection tunnel 620. Suspected contraband, if found in the car 200 during the image analysis, then the inspector can print information via a printer at an exit room 616. FIG. 6 shows the wall details such as concrete base 606 (802) being the outer most walls that extend to x-ray tunnel frame 602 (806) and x-ray tunnel frame 614 (804).

Rubbery conveyor belt 622 which is enhanced by the steel bars and electrical motors in the terminals has the ability to support and transport a motorized vehicle at 5 tons weight into the detection tunnel 620. The conveyor belt 622 can be comprised of two separated main sections with a small hole in between, which can allow the penetration of the x-ray to the fixed detectors below the longitudinal vacuum which can detect the x-ray penetrating the body of the motorized vehicle and emitting downward so that there are no objects which prevent the x-ray penetrations of the motorized vehicle to be detected and to provide a clear image of the motorized vehicle and its contents.

There is a conveyor belt 216, 622 which moves in one direction continuously at fixed speed of 0.2 m/sec, for instance, which can enhance the flexibility of the flow of the motorized vehicles to be detected without any need to return back the conveyor to the system entry to hold the next motorized vehicle. A conveyor belt which comprises of many sections, whereas each section can be controlled with respect to speed separately.

In addition, it will be appreciated that the various apparatuses, method and system disclosed herein may be embodied using means for achieving the various combinations of scanning various objects, vehicles, motorized vehicle and other transported goods for security inspection in a fast and efficient way. Accordingly, the specification and drawings are to be regarded in an illustrative rather than a restrictive sense.

What is claimed is:

1. An apparatus for inspecting a motorized vehicle, comprising:
    a concrete housing having a specific conveyor belt configured to move the motorized vehicle at a specific speed for a security inspection;
    a first x-ray beam source mounted at a side of the specific conveyor belt, inside the concrete housing, the first x-ray beam source being configured to emit a first x-ray beam, from beside the motorized vehicle, at a divergence angle of 60 degrees toward the motorized vehicle on the specific conveyor belt when the motorized vehicle is at a predetermined scanning point; and
    a second x-ray beam source mounted to an inside surface of a roof of the concrete housing and configured to emit a second x-ray beam, from above the motorized vehicle, at a divergence angle of 40 degrees toward the motorized vehicle on the specific conveyor belt at the predetermined scanning point,
    wherein the first and second x-ray beams cover an entirety of a cross-section of the motorized vehicle, and each of the first and second x-ray beams is emitted at a specific energy range to the motorized vehicle,
    wherein the specific energy range for each of the first and second x-ray beams is selected from a range of 3.8 MeV to 6 MeV, and
    wherein each of the first and second x-ray beam sources has a corresponding x-ray detector on an opposite side of the motorized vehicle, in order to detect inside said motorized vehicle a specific object, material, or contraband that is a security threat.

2. The apparatus of claim 1, wherein the specific conveyer belt is made of a rubber and steel having two longitudinal sections that are 5 mm apart to allow the second x-ray beam to pass through them.

3. The apparatus of claim 1, wherein the motorized vehicle is one of a car or a truck.

4. The apparatus of claim 1, wherein the specific speed of the motorized vehicle through the concrete housing is a speed in a range from 0.1 m/s to 0.3 m/s.

5. The apparatus of claim 4, wherein the specific speed of the motorized vehicle through the concrete housing is 0.2 m/s.

6. The apparatus of claim 1, wherein the specific object, material, or contraband is organic or inorganic in nature.

7. A method for inspecting a motorized vehicle, comprising:
    passing the motorized vehicle under a concrete housing equipped with a two x-ray imaging system having:
        a first x-ray beam source mounted at a side of a specific conveyor belt, inside the concrete housing, the first x-ray beam source being configured to emit a first x-ray beam, from beside the motorized vehicle, toward the motorized vehicle on the specific conveyor belt when the motorized vehicle is at a predetermined scanning point, and
        a second beam source mounted to an inside surface of a roof of the concrete housing and configured to emit a second x-ray beam, from above the motorized vehicle, toward the motorized vehicle on the specific conveyor belt at the predetermined scanning point,
        wherein the two x-ray imaging system is configured to screen for organic and/or inorganic matter present in the motorized vehicle, wherein said matter is prohibited by law from being carried in said motorized vehicle; and
    emitting the first x-ray beam and the second x-ray beam at a specific energy value and at a specific source to object distance range to penetrate a specific thickness of the motorized vehicle to detect whether the organic or inorganic matter is present in the motorized vehicle,
    wherein each of the first x-ray beam and the second x-ray beam has the specific energy value in a range from 3.8 MeV to 6 MeV, and
    wherein the second x-ray beam covers an entire cross-section of the motorized vehicle.

8. The method of claim 7, wherein the motorized vehicle is one of a car or a truck.

9. The method of claim 7, wherein the specific thickness of the motorized of the motorized vehicle is 240 mm or less.

10. A method for inspecting motorized vehicles, comprising:
    placing a motorized vehicle on a specific conveyor belt, said specific conveyor belt moving at a specific speed in an enclosed concrete housing;
    activating each of a first x-ray beam source mounted at a side of the specific conveyor belt, inside the concrete housing, the first x-ray beam source being configured to emit a first x-ray beam, from beside the motorized vehicle, toward the motorized vehicle on the specific conveyor belt when the motorized vehicle is at a predetermined scanning point, and a second beam source mounted to an inside surface of a roof of the concrete housing and configured to emit a second x-ray beam, from above the motorized vehicle, toward the motorized vehicle on the specific conveyor belt at the predetermined scanning point, wherein the first x-ray beam source and the second x-ray beam source are part of a two x-ray imaging system configured to scan the motorized vehicle for at least one of an organic and an inorganic material, wherein the first x-ray beam and the second x-ray beam are emitted at a specific energy value, a specific source to object distance range, and a specific angle with respect to the motorized vehicle to penetrate a specific thickness of the motorized vehicle, wherein each of the first x-ray beam and the second x-ray beam has the specific energy value in a range from 3.8 MeV to 6 MeV; and detecting an absence and/or a presence of said organic material and/or said inorganic material in the motorized vehicle.

11. The method of claim 10, further comprising:

proceeding to move the motorized vehicle to an exit gate if there is an absence of said organic material and/or said inorganic material detected in the motorized vehicle, or proceeding to move the motorized vehicle to an area for a physical inspection if there is a presence of said organic material and/or said inorganic material detected in the motorized vehicle.

12. The method of claim 10, wherein the motorized vehicle is one of a car or a truck.

13. The method of claim 10, wherein the specific speed of the motorized vehicle through the concrete housing is a speed in a range from 0.1 m/s to 0.3 m/s.

14. The method of claim 13, wherein the specific movement speed of the motorized vehicle through the concrete housing is 0.2 m/s.

15. The method of claim 10, wherein the specific thickness of the motorized vehicle is 240 mm or less.

* * * * *